United States Patent
Weisman et al.

(10) Patent No.: US 9,255,853 B2
(45) Date of Patent: Feb. 9, 2016

(54) NON-CONTACT STRAIN SENSING OF OBJECTS BY USE OF SINGLE-WALLED CARBON NANOTUBES

(71) Applicants: R. Bruce Weisman, Houston, TX (US); Paul A. Withey, League City, TX (US); Sergei M. Bachilo, Houston, TX (US); Satish Nagarajaiah, Sugar Land, TX (US); Venkata Srivishnu M. Vemuru, Houston, TX (US)

(72) Inventors: R. Bruce Weisman, Houston, TX (US); Paul A. Withey, League City, TX (US); Sergei M. Bachilo, Houston, TX (US); Satish Nagarajaiah, Sugar Land, TX (US); Venkata Srivishnu M. Vemuru, Houston, TX (US)

(73) Assignee: WILLIAM MARSH RICE UNIVERSITY, Houston, TX (US)

(*) Notice: Subject to any disclaimer, the term of this patent is extended or adjusted under 35 U.S.C. 154(b) by 0 days.

(21) Appl. No.: 14/398,799

(22) PCT Filed: Mar. 14, 2013

(86) PCT No.: PCT/US2013/031527
§ 371 (c)(1),
(2) Date: Nov. 4, 2014

(87) PCT Pub. No.: WO2013/184212
PCT Pub. Date: Dec. 12, 2013

(65) Prior Publication Data
US 2015/0115159 A1 Apr. 30, 2015

Related U.S. Application Data

(60) Provisional application No. 61/642,573, filed on May 4, 2012.

(51) Int. Cl.
*G01J 5/02* (2006.01)
*G01L 1/24* (2006.01)
(Continued)

(52) U.S. Cl.
CPC . *G01L 1/248* (2013.01); *G01L 1/25* (2013.01); *G01N 21/359* (2013.01); *G01N 2201/06113* (2013.01); *G01N 2203/0629* (2013.01); *G01N 2203/0652* (2013.01)

(58) Field of Classification Search
CPC .......................................................... G01J 5/02
See application file for complete search history.

(56) References Cited

U.S. PATENT DOCUMENTS 7,730,547 B2 * 6/2010 Barrera et al. .................. 850/21
2004/0061858 A1 4/2004 Pope et al.
(Continued)

OTHER PUBLICATIONS

International Search Report and Written Opinion for PCT/US2013/031527, Mailed on Dec. 6, 2013.
(Continued)

*Primary Examiner* — David Porta
*Assistant Examiner* — Faye Boosalis
(74) *Attorney, Agent, or Firm* — Winstead PC (57) ABSTRACT

In some embodiments, the present invention provides methods of detecting strain associated with an object by: (1) irradiating a composition that has been applied to the object, where the composition comprises semiconducting single-walled carbon nanotubes; (2) measuring an emission from the irradiated composition, where the emission comprises near infrared emission; and (3) correlating the near infrared emission to the presence or absence of strain associated with the object. In some embodiments, the aforementioned steps occur without physically contacting the object or the composition. In some embodiments, the aforementioned steps occur without utilizing Raman spectroscopy. Further embodiments of the present invention also include a step of applying the composition to the object.

32 Claims, 5 Drawing Sheets

(51) Int. Cl.
*G01L 1/25* (2006.01)
*G01N 21/359* (2014.01)

(56) References Cited

U.S. PATENT DOCUMENTS

| | | | |
|---|---|---|---|
| 2006/0071165 A1* | 4/2006 | Tenne et al. | 250/309 |
| 2006/0253942 A1 | 11/2006 | Barrera et al. | |
| 2007/0292896 A1 | 12/2007 | Strano et al. | |
| 2010/0141939 A1 | 6/2010 | Zhan | |
| 2010/0170015 A1 | 7/2010 | Park et al. | |
| 2010/0279421 A1 | 11/2010 | Strano et al. | |
| 2010/0323925 A1 | 12/2010 | Gabriel et al. | |
| 2011/0089958 A1 | 4/2011 | Malecki et al. | |
| 2011/0137577 A1 | 6/2011 | Chen et al. | |
| 2011/0321204 A1 | 12/2011 | Karaki et al. | |

OTHER PUBLICATIONS

Li et al., "Carbon Nanotube Film Sensors", Adv. Mater., 2004, vol. 16, No. 7, pp. 640-643.
Dharap et al., "Nanotube film based on single-wall carbon nanotubes for strain sensing", Nanotechnology, 2004, 15, 379-382.
Leeuw et al., "Strain Measurements on Individual Single-Walled Carbon Nanotubes in a Polymer Host: Structure-Dependent Spectral Shifts and Load Transfer", Nano Lett., 2008, vol. 8, No. 3, 826-831.
Bachilo et al., Structure-Assigned Optical Spectra of Single-Walled Carbon Nanotubes, Science 2002, 298, 2361-2366.
O'Connell et al., Band Gap Fluorescence from Individual Single-Walled Carbon Nanotubes, Science 2002, 297, 593-596.
Weisman et al., Dependence of Optical Transition Energies on Structure for Single-Walled Carbon Nanotubes in Aqueous Suspension: An Empirical Kataura Plot, Nano Lett. 2003, 3, 1235-1238.
Minot et al., Tuning Carbon Nanotube Band Gaps with Strain, Phys. Rev. Lett. 2003, 90, 156401-1-156401-4.
Vemuru et al., Strain sensing using a multiwalled carbon nanotube film, J. Strain Analysis 2009, 44, 555-562.
Srivastava et al., The strain sensing and thermal-mechanical behavior of flexible multi-walled carbon nanotube/polystyrene composite films, Carbon 2011, 49, 3928-3936.
Miyauchi et al., Cross-polarized optical absorption of single-walled nanotubes by polarized photoluminescence excitation spectroscopy, S. Phys. Rev. B 2006, 74, 205440.
Yang et al., Electronic Structure of Deformed Carbon Nanotubes, J. Phys. Rev. Lett. 2000, 85, 154-157.
Li et al., Chirality Assignment of Single-Walled Carbon Nanotubes with Strain, Phys. Rev. Lett. 2004, 93, 156104-1-156104-4.
Maki et al., Direct Observation of the Deformation and the Band Gap Change from an Individual Single-Walled Carbon Nanotube under Uniaxial Strain, Nano Lett. 2007, 7, 890-895.
Huang et al., Direct Measurement of Strain-Induced Changes in the Band Structure of Carbon Nanotubes, J. Phys. Rev. Lett. 2008, 100, 136803-1-136803-4.
Valavala et al., Self-consistent calculations of strain-induced band gap changes in semiconducting (n,0) carbon nanotubes, Phys. Rev. B 2008, 78, 235430-1-235430-6.
Lefebvre et al., Photoluminescence from an individual single-walled carbon nanotube, Phys. Rev. B 2004, 69, 075403-1-075403-5.
Casey et al., Chirality-Resolved Length Analysis of Single-Walled Carbon Nanotube Samples through Shear-Aligned Photoluminescence Anisotropy, ACS Nano 2008, 2, 1738-1746.
Arnold et al., Sorting carbon nanotubes by electronic structure using density differentiation, Nature Nanotech. 2006, 1, 60-65.
Ghosh et al., Advanced sorting of single-walled carbon nanotubes by nonlinear density-gradient ultracentrifugation, Nature Nanotech. 2010, 5, 443-450.

* cited by examiner

NON-CONTACT STRAIN SENSING OF OBJECTS BY USE OF SINGLE-WALLED CARBON NANOTUBES

CROSS-REFERENCE TO RELATED APPLICATIONS

This application claims priority to U.S. Provisional Patent Application No. 61/642,573, filed on May 4, 2012. The entirety of the aforementioned application is incorporated herein by reference.

STATEMENT REGARDING FEDERALLY SPONSORED RESEARCH

This invention was made with government support under Grant No. CHE-1112374, awarded by the National Science Foundation; and Grant No. FA8650-05-D-5807, awarded by the U.S. Department of Defense. The government has certain rights in the invention.

BACKGROUND

Current methods of monitoring strain on various structures have numerous limitations in terms of efficacy, predictability, reliability, and flexibility. Therefore, a need exists for improved methods of monitoring strain on various objects. The present disclosure addresses this need.

SUMMARY

In some embodiments, the present disclosure provides methods of detecting strain associated with an object. In some embodiments, such methods generally include: (1) irradiating a composition that has been applied to the object, where the composition comprises semiconducting single-walled carbon nanotubes; (2) measuring an emission from the irradiated composition, where the emission comprises near infrared emission; and (3) correlating the near infrared emission to the presence or absence of strain associated with the object. In some embodiments, the aforementioned steps occur without physically contacting the object or the composition. In some embodiments, the aforementioned steps occur without utilizing Raman spectroscopy.

In addition, various methods may be used to irradiate the composition that has been applied to the object. For instance, in some embodiments, the irradiation occurs by use of a light source. In some embodiments, the light source may include at least one of lasers, light emitting diodes, incoherent light, polarized light, unpolarized light, and combinations thereof. In some embodiments, the light source may include polarized light.

Various methods may also be used to measure the near infrared emission from the irradiated composition. For instance, in some embodiments, the measuring of the emission occurs by optical infrared spectrometry.

In addition, various methods may be used to correlate the measured near infrared emission to the presence or absence of strain associated with the object. In some embodiments, the presence or absence of strain is determined as a function of a spectral shift of the semiconducting single-walled carbon nanotubes in the composition, where the spectral shift is indicative of strain. In some embodiments, the spectral shift includes a spectral shift in an emission peak of the carbon nanotubes.

The methods of the present disclosure may also be used to detect strain on various objects. For instance, in some embodiments, the objects may include at least one of concrete, steel, metals, alloys, non-metallic composites, pipes, pavements, vessels, engines, optical fibers, and combinations thereof.

Further embodiments of the present disclosure may also include a step of applying the composition to the object. In some embodiments, the applying may include spraying, coating, spray coating, shift coating, spin coating, dip coating, printing, brushing, and combinations thereof.

Furthermore, the compositions of the present disclosure may be applied to various regions of objects. For instance, in some embodiments, the compositions of the present disclosure may be applied to one or more surfaces of an object in order to determine the presence or absence of strain on the one or more surfaces of the object. In some embodiments, the composition may be applied to an internal cavity of an object in order to determine the presence or absence of strain on the one or more internal cavities of the object. In some embodiments, the composition may be applied to one or more edges of an object in order to determine the presence or absence of strain on the one or more edges of the object.

As set forth in more detail herein, the methods of the present disclosure provide numerous applications and advantages. For instance, the methods of the present disclosure can allow for the quick and precise strain measurements of various objects at any position and along any direction without the need for physically contacting the objects or utilizing Raman spectroscopy.

BRIEF DESCRIPTION OF THE FIGURES

FIG. 1A provides a diagram of an apparatus for measuring strain associated with the object. FIG. 1B provides a more detailed diagram of the apparatus in FIG. 1A. FIG. 1C provides a depiction of SWCNT angle definitions for strain measurement.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Operational safety of various objects, such as aircraft, bridges, and buildings, requires periodic strain monitoring of key structural elements within the objects. Such monitoring helps avoid or predict structural collapses or failures. Existing methods for measuring strain involve implanted macroscopic sensors that report strains at fixed positions and along fixed directions through physical connections to external readout devices. Such sensors provide a relatively coarse sampling of the substrate's strain field. Furthermore, their presence can disrupt the function of the object being monitored. Thus, new methods are required for monitoring the strain associated with various objects.

In some embodiments, the present disclosure provides novel methods of detecting strain associated with an object. In some embodiments, such methods include: (1) irradiating a composition that has been applied to the object, where the composition comprises single-walled carbon nanotubes (e.g., semiconducting single-walled carbon nanotubes); (2) measuring an emission from the irradiated composition (e.g., near infrared emission); and (3) correlating the measured emission to the presence or absence of strain associated with the object. The aforementioned steps are based on Applicants' findings that strain associated with an object can be transmitted through the composition and deform the single-walled carbon nanotubes in the composition. This in turn leads to changes in the electronic structures of the single-walled carbon nanotubes, which can then be measured optically in various ways, such as strain-induced near-infrared spectral shifts of the single-walled carbon nanotubes.

In some embodiments, the aforementioned steps of irradiating, measuring and correlating occur without physically contacting the object or the composition. In some embodiments, the aforementioned methods occur without utilizing Raman spectroscopy. In additional embodiments, the methods of the present disclosure may also include a step of applying the compositions to an object.

More specific embodiments of the methods of the present disclosure can be illustrated with reference to apparatus 10 in FIGS. 1A and 1B. In such embodiments, apparatus 10 is utilized to detect strain associated with object 16, which is coated with a composition 18 that contains randomly dispersed semiconducting single-walled carbon nanotubes 38.

Apparatus 10 generally includes laser source 12 and near infrared (NIR) spectrometer 22. As illustrated in FIG. 1B, laser source 12 can be associated with attenuation filter 15 and half-wave retardation plate 13. In addition, NIR spectrometer 22 can be associated with fiber collimator 26 and long-pass filter 28 through optical fiber 24. In addition, both NIR spectrometer 22 and laser source 12 can be associated with dichroic reflector 30 and lens 32. In addition, for testing purposes, object 16 can be immobilized onto strain jig 34 and associated with resistive strain gage 39 and strain gage readout device 36 (as shown).

In operation, laser source 12 irradiates composition 18 on object 16 through laser 14. This in turn leads to near infrared emission 20 from the irradiated composition. Thereafter, near infrared emission 20 is detected and analyzed by NIR spectrometer 22. The measured emission is then correlated to the presence or absence of strain associated with object 16. For instance, in some embodiments, the presence or absence of strain associated with object 16 is detected as a function of a spectral shift of semiconducting single-walled carbon nanotubes 38 in composition 16, where the spectral shift is indicative of strain.

As described in more detail herein, the methods of the present disclosure can have various embodiments. For instance, various methods may be used to irradiate compositions that have been applied to objects. Furthermore, various methods may be used to measure an emission from the irradiated compositions. Likewise, various methods may be utilized to correlate the measured emission to the presence or absence of strain associated with the object. Moreover, various compositions may be applied to various objects by various methods.

Compositions

The compositions of the present disclosure generally include one or more types of single-walled carbon nanotubes. In various embodiments, the compositions of the present disclosure may also include one or more polymeric or non-polymeric additives.

Single-Walled Carbon Nanotubes

The compositions of the present disclosure generally include single-walled carbon nanotubes (SWCNTs). In some embodiments, the compositions of the present disclosure include semiconducting single-walled carbon nanotubes. By way of information, SWCNTs are a family of highly elongated tubular structures composed of carbon atoms covalently bonded into specific ordered forms. Each form has a well-defined diameter and roll-up angle, and is uniquely labeled by a pair of integers, (n,m). Among the optimal properties of SWCNTs are their well-defined spectral transitions that vary systematically with physical structure, reflecting the quantum confinement of $\pi$-electrons perpendicular to the tube axis. Most SWCNT structural species are semiconducting and show robust photoluminescence (fluorescence emission) at distinct near-IR wavelengths corresponding to their semiconducting band gaps.

It is known from theory and experiment that axial stretching or compression of SWCNTs causes predictable changes in electronic structure that systematically shift their spectral transitions. Previous studies on individual nanotubes have confirmed that these shifts occur in opposite directions for "mod 1" and "mod 2" nanotubes (for which mod (n−m, 3)=1 or 2), and that the magnitudes of the spectral shifts are proportional to cos (3θ), where θ is the nanotube roll-up angle. These shifts in SWCNT fluorescence spectra can be large enough in some embodiments to reveal axial strains below 0.1%.

The single-walled carbon nanotubes in the compositions of the present disclosure may be in various states. For instance, in some embodiments, the single-walled carbon nanotubes may include pristine single-walled carbon nanotubes, functionalized single-walled carbon nanotubes, un-functionalized single-walled carbon nanotubes, and combinations thereof.

In more specific embodiments, the single-walled carbon nanotubes in the compositions of the present disclosure may include pristine semiconducting single-walled carbon nanotubes. In particular, it may be desirable in some embodiments for the single-walled carbon nanotubes to be pristine in order to provide bright near-IR fluorescence.

In other embodiments, the single-walled carbon nanotubes in the compositions of the present disclosure may include functionalized single-walled carbon nanotubes. In some embodiments, the single-walled carbon nanotubes may be functionalized with one or more functionalizing agents. In some embodiments, the functionalizing agents may include, without limitation, phenyl groups, aniline groups, alkanes, alkyl groups, aryl groups, tert-butyl groups, alkenyl groups, alkynyl groups, ester groups, carboxyl groups, halogens, metals, metal oxides, metal sulfides, sulfate groups, and combinations thereof.

In some embodiments, the single-walled carbon nanotubes of the present disclosure may include structurally selected single-walled carbon nanotubes. In some embodiments, the single-walled carbon nanotubes are structurally selected based on at least one of chirality, length, diameter, and combinations thereof. For instance, in some embodiments, the single-walled carbon nanotubes in the composition are structurally selected based on chirality. In more specific embodiments, the single-walled carbon nanotubes in the composition are structurally selected based on specific (n, m) structures.

The single-walled carbon nanotubes in the compositions of the present disclosure may also be in various formations. For instance, in some embodiments, the single-walled carbon nanotubes in the compositions may include individualized single-walled carbon nanotubes. In some embodiments, the single-walled carbon nanotubes in the compositions may include randomly dispersed single-walled carbon nanotubes, such as single-walled carbon nanotubes that have random in-plane angles ($\phi$). In particular, randomly dispersed single-walled carbon nanotubes can provide an emission spectrum that is broadened and less shifted in peak position than the same single-walled carbon nanotubes aligned parallel to a strain axis and parallel to a surface of an object.

In some embodiments, the single-walled carbon nanotubes in the compositions of the present disclosure may be unidirectionally aligned in the compositions. In some embodiments, the single-walled carbon nanotubes may be aligned along the polarization axis. For instance, in some embodiments, emission may be strongest for those single-walled carbon nanotubes aligned along the polarization axis, as the dominant nanotube spectral transitions may be highly anisotropic.

Polymers

The compositions of the present disclosure may also include various polymers. Suitable polymers may include, without limitation, polyethylenes, polypropylenes, polystyrenes, polyamides, polyimides, epoxies, polyvinyl alcohols, polybutadienes, poly acrylic acids, poly lactic acids, poly methacrylic acids, polymethyl methacrylates, polyurethanes, poly vinyl chlorides, polycarbonates, cyanoacrylates, and combinations thereof. In more specific embodiments, the compositions of the present disclosure may include polyurethane.

Additional Contents

In various embodiments, the compositions of the present disclosure may also include additional contents, such as solvents, surfactants, additives, and the like. The contents of the compositions of the present disclosure are not limiting. However, it is desirable for the contents to not strongly attenuate the red and near-IR wavelengths of nanotube excitation and emission transitions. It is also desirable that the contents of the compositions not significantly quench the intrinsic fluorescence of embedded carbon nanotubes. It also desirable that the contents of the compositions support dispersions of individualized SWCNTs. It is also desirable that the contents of the compositions show strong interfacial adhesion, mechanical durability, and environmental durability.

In various embodiments, a thin protective coating may also be applied over the compositions of the present disclosure. In some embodiments, such a protective coating can provide additional resistance to damage from harsh environments, such as underwater environments in various embodiments. For instance, in some embodiments, a protective coating may be applied over a layer containing strain-sensing SWCNTs.

Application of Compositions to Objects

In some embodiments, the compositions of the present disclosure may be applied to objects by various methods. For instance, in some embodiments, the application may include at least one of spraying, coating, spray coating, shift coating, spin coating, dip coating, printing, brushing, and combinations thereof. In more specific embodiments, the compositions of the present disclosure may be applied to objects by spin coating.

In some embodiments, various coating enhancements could be implemented to effectively modify the SWCNT orientations and/or alignments. In some embodiments, the enhancements may be effected through the rheological properties of the supporting polymer matrix. For instance, in some embodiments, multiple SWCNT layers may be deposited on an object in which individual layers are oriented in particular directions of interest to enhance measurement sensitivity in those directions.

In more specific embodiments, the compositions of the present disclosure may be in pre-fabricated form. In such embodiments, the compositions may be applied to objects by adhesion. In some embodiments, the pre-fabricated compositions may be adhered to objects by the utilization of various bonding agents. For instance, the compositions of the present disclosure may be deposited in a variety of configurations onto a supporting medium, such as a polyimide or other plastic or polymer foil that is subsequently attached to test part(s) in question (e.g., a position on an object).

In some embodiments, the compositions of the present disclosure may be in the form of rolls, sheets, or pre-cut decals. In more specific embodiments, such compositions may be self-adhesive or require the use of an application-specific adhesive material to secure them to test parts in question (e.g., a position on an object).

In further embodiments, one or more meta-data, such as position or other identifiers in the form of decals, may become associated with the compositions of the present disclosure. For instance, in some embodiments, the meta-data could be in the form of bar codes, radio-frequency identification (RFID), and other machine readable methods and media. In additional embodiments, these decals may have non-adhered unstressed regions that can serve as reference locations to permit automated compensation for temperature and age-induced drifts.

Furthermore, the compositions of the present disclosure may have various thicknesses on the applied objects. For instance, in some embodiments, the composition that is applied to the object has a thickness that ranges from about 1 µm to about 1 mm. In some embodiments, the composition that is applied to the object has a thickness that ranges from about 10 µm to about 500 µm. In some embodiments, the composition that is applied to the object has a thickness of about 25 µm.

In addition, the compositions of the present disclosure may be applied to various regions of objects for strain detection on those regions. For instance, in some embodiments, the compositions of the present disclosure may be applied to one or more surfaces of an object for strain detection on those surfaces. In some embodiments, the compositions of the present disclosure may be applied to one or more internal cavities of an object for strain detection on one or more of those internal cavities. In some embodiments, the compositions of the present disclosure may be applied to one or more edges of an object for strain detection on one or more of the edges.

In some embodiments, the compositions of the present disclosure may coat an entire surface of an object. In some embodiments, the compositions of the present disclosure may coat an entire object. In some embodiments, the compositions of the present disclosure may partially coat an object or a surface of an object. In some embodiments, the compositions of the present disclosure may be uniformly coated on an object. In some embodiments, the compositions of the present disclosure may be unevenly coated on an object. In some embodiments, the compositions of the present disclosure may serve dual roles as adhesives and strain-sensing media.

Objects

The compositions of the present disclosure may be applied to various objects for strain detection on those objects. For instance, in some embodiments, the objects may include, without limitation, concrete, steel, metals, alloys, non-metallic composites, pipes, pavements, vessels, engines, optical fibers, and combinations thereof. More specific objects can include, without limitation, pipelines, airframe components, buildings, high pressure gas tanks, containment vessels, engines, motors, moving parts, optical fibers, and the like.

In further embodiments, the compositions of the present disclosure may be applied to transparent objects, or objects that have transparent elements or components. In some embodiments, the transparent objects may include, without limitation, lenses, windows, windscreens, portholes, viewing ports, aircraft canopies, and combinations thereof.

Additional objects can also be envisioned. Furthermore, as set forth in more detail herein, various methods may be utilized to detect strain associated with objects through irradiation, emission measurement, and correlation of the measured emission to strain.

Irradiation of Compositions

Various methods may be utilized to irradiate the compositions of the present disclosure. For instance, in some embodiments, the irradiation occurs by the use of a light source. In some embodiments, the light source may include lasers, light emitting diodes, incoherent light, polarized light, unpolarized light, and combinations thereof.

In some embodiments, the light source includes polarized light. In some embodiments, the polarized light may be derived from a laser, such as a diode laser. In more specific embodiments, the light source may include a linearly polarized 660 nm light from a 70 mW, circularized-beam diode laser (PTI model PPM80). Additional light sources can also be envisioned. For instance, in various embodiments, irradiation and detection may be accomplished by utilizing optical fibers, fiber probes, and integrated optical elements.

Measuring Emission from Irradiated Compositions

The irradiated compositions may emit various forms of emissions. For instance, in some embodiments, the emission may include near-infrared emission, such as near infrared fluorescence. In some embodiments, the near infrared fluorescence may include wavelengths that range from about 750 nm to about 1.5 µm.

In addition, various methods may be used to measure emission from the irradiated compositions. For instance, in some embodiments, the measuring step may include the use of optical spectrometry, such as optical infrared spectrometry.

Detecting Presence or Absence of Strain

Without being bound by theory, it is envisioned that strain associated with the objects of the present disclosure deforms the single-walled carbon nanotubes in the compositions. This in turn causes predictable changes in the electronic structures of the deformed single-walled carbon nanotubes. These changes can then measured optically by various methods.

In some embodiments, the presence or absence of strain associated with an object is determined as a function of a spectral shift of the single-walled carbon nanotubes in the composition, where the spectral shift is indicative of strain. In more specific embodiments, the spectral shift may include a spectral shift in an emission peak of the single-walled carbon nanotubes in the composition.

In various embodiments, spectral shifts can be determined by computer programs that relate peaks in emission spectra to particular SWCNT (n,m) structures and use numerical curve fitting methods to precisely determine the spectral positions of those peaks. Spectral separations between specific combinations of peaks are then compared to theoretical models and empirical calibration data to deduce strain magnitudes. Strain values deduced for several different polarization directions of the irradiating light are numerically analyzed to determine the axis of maximum strain. It is also envisioned that wavelength-modulated, amplitude-modulated, and/or polarization-modulated irradiation could be used to facilitate discrimination of the SWCNT emission from background radiation so as to enhance the signal-to-noise ratio of spectra from the strain-sensing composition.

Applications and Advantages

The methods of the present disclosure provide numerous applications and advantages. For instance, the methods of the present disclosure can allow for the quick and precise strain measurement of various objects at any position, and along any direction. For instance, by rotating a polarization axis of an excitation light, strain can be quantitatively deduced at any position and along any direction of an object.

Likewise, Applicants' methods can allow for the mapping of a strain field over a wide area of an object by moving an optical system to each point of interest and capturing emission spectra for several polarization settings of the excitation beam. As such, the methods of the present disclosure can be used to detect strain on surfaces, edges, or internal cavities of objects. In more specific embodiments, the methods of the present disclosure can be used to detect internal strain on objects, such as subsurface strain.

Furthermore, the methods of the present disclosure can be utilized to detect low levels of strain. For instance, in some embodiments, the methods of the present disclosure can be used to detect strains of less than about 1%, less than about 0.6%, less than about 0.2%, or less than about 0.1%.

The methods of the present disclosure also provide a simpler alternative to current strain-sensing methods of objects. For instance, the methods of the present disclosure do not require physical contact with objects to be analyzed. Furthermore, optical emission spectroscopy requires no electrical connections and provides stronger signals and faster data acquisition than Raman spectroscopy. Thus, the methods of present disclosure provide improved alternatives to carbon nanotube-based sensors that involve strain-induced changes in electrical transport properties or Raman spectra.

As such, Applicants envision the use of the methods of the present disclosure in various objects, systems and settings. For instance, the methods of the present disclosure can be used to detect strain in mechanical systems, structural systems, and electrical systems. Likewise, the methods of the present disclosure can be used to detect strain for various industries, including the civil engineering industry, the aerospace industry, the defense industry, electronic industries, energy industries, and the like.

Furthermore, the methods of the present disclosure may be used to detect strain for various purposes, including the measurement of vibrations, oscillatory deformations, dynamic strain, and amplitudes. The methods of the present disclosure can also be used to study the long term effects of strain on an object. The methods of the present disclosure can also be used to count the number of strains on an object.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1

Non-Contact Strain Measurement Using Single-Walled Carbon Nanotube Composite Coatings This Example demonstrates that composite coatings have been developed that reveal strains in underlying structural elements through non-contact optical measurement. Dilute individualized single-walled carbon nanotubes are embedded in a polymeric host and applied to form a thin coating. Strain in the substrate is transmitted through the polymer to the nanotubes, causing systematic and predictable spectral shifts of the nanotube near-infrared fluorescence peaks.

In particular, this example demonstrates a novel non-contact method for strain monitoring based on the spectral properties of single-walled carbon nanotubes (SWCNTs). In this Example, SWCNTs are unobtrusively embedded in a thin polymeric coating applied to the substrate of interest. Strain in the substrate is transmitted through the coating, deforming the embedded nanotubes and causing predictable changes in their electronic structure. These changes are measured optically, without physical contact, as strain-induced spectral shifts of the characteristic SWCNTs near-IR fluorescence peaks.

First, a structural element of interest is coated with a thin polymeric film containing dilute individualized SWCNTs. If the coating adheres strongly to the substrate and to the embedded nanotubes, then strain in the coating will match that of the substrate, and embedded nanotubes will be axially deformed by the spatial projection of the coating strain along the nanotube axis. The nanotube strain at a position of interest can be quantitatively monitored by irradiating the surface with a visible laser of suitable wavelength and capturing the resulting near-IR fluorescence for spectral interpretation.

Methods

Raw SWCNTs grown in the Rice University HiPco reactor were weighed and added to a commercial exterior varnish (Minwax Helmsman 350 VOC Spar Urethane) at a weight percent of approximately 0.02%. The mixture was tip ultrasonicated at a power of about 10 W (15 s on, 15 s off duty cycle) for 10 to 30 min until the SWCNTs appeared thoroughly dispersed in the polymer. The SWCNT-polyurethane mixture was then spin-coated onto a PMMA substrate (75× 25×6 mm) that had been surface-roughened using a fine sandpaper to improve adhesion, and allowed to dry under ambient conditions. Spin coating was repeated until the SWCNT fluorescence emission from the surface coat was conveniently intense, and then the sample was cured for one to two weeks at room temperature prior to measurements. Applicants observed that the time needed for proper curing increased directly with the film thickness. Final coating thicknesses were approximately 25 μm.

Figure 1:
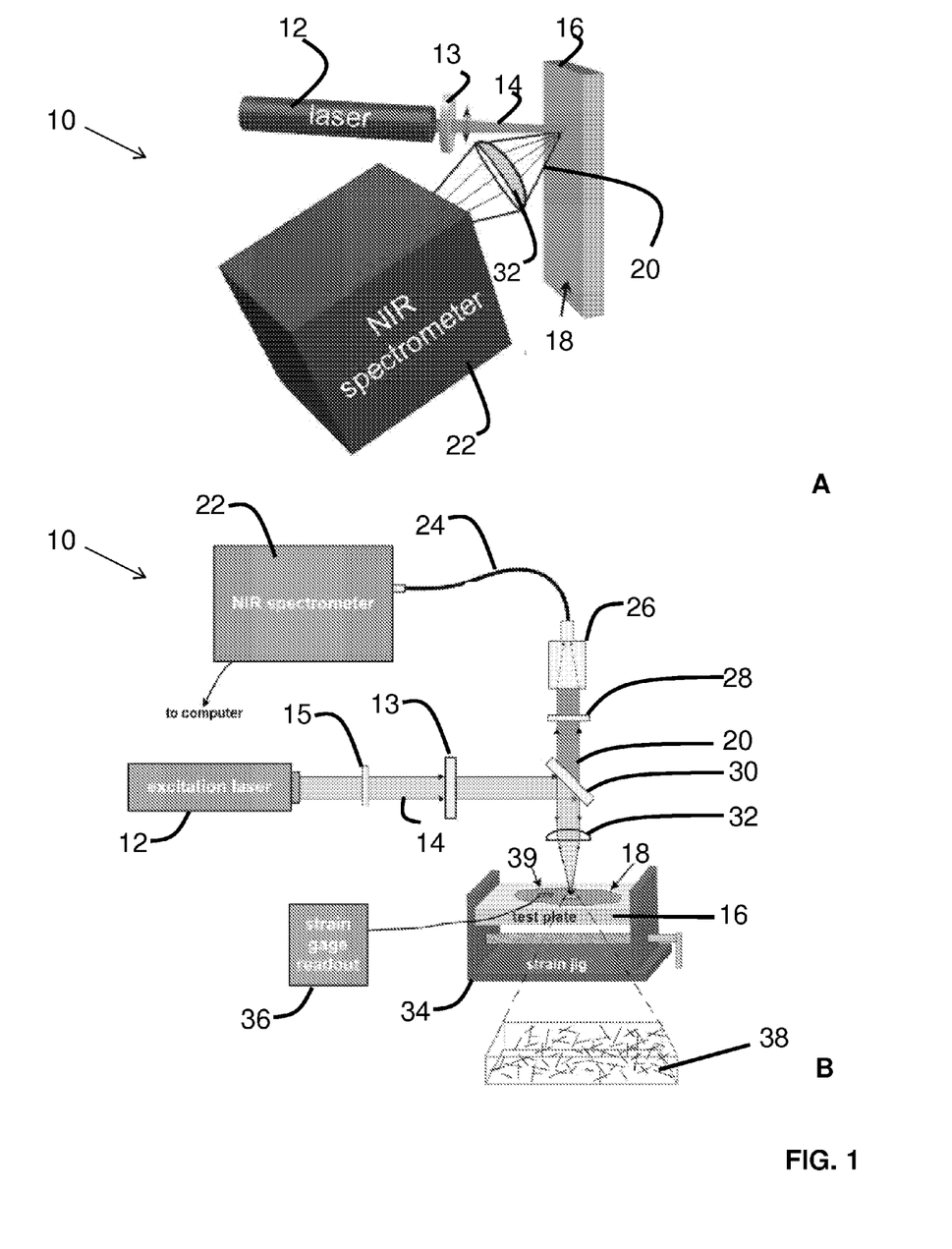
FIG. 1 provides exemplary schemes and diagrams for measuring strain associated with an object that has been coated with a composition containing semiconducting single-walled carbon nanotubes (SWCNTs).

As illustrated in FIG. 1B, the sample 16 was subjected to strain using a custom built four-point bending jig 34. Strain in the nanocomposite film close to the focus of the interrogating laser 12 was measured by a resistive foil strain gage 39 affixed to the film. Strain in the PMMA bar was measured using a second strain gage mounted at the corresponding location on the opposite surface of the PMMA bar. Applicants monitored readings from the gages in real time to check for any relaxation of the polymer surface. The applied strain (measured on the PMMA bar) and strain in the polymer film were found to be nearly equal for thin polymer layers prepared by spin coating. Applicants' bending jig 34 was manually adjusted to give strain increments of 0.05% during loading and unloading.

SWCNT fluorescence was excited with polarized 660 nm light from a 70 mW, circularized-beam diode laser 12 (PTI model PPM80). As shown in FIGS. 1A and 1B, the laser beam was passed through a Schott KG3 filter 15 to remove near-IR components and a half-wave plate 13 to allow adjustment of its polarization plane. It was then focused onto the sample with a 30 mm focal length lens 32. Sample fluorescence was collected either in the forward direction, after passing through the transparent substrate, or in the backward direction, as in FIG. 1B.

The emission passed through an 850 nm long-pass filter 28 to block stray excitation light and was then coupled into a multi-mode optical fiber 24 that terminated at the entrance slit of a near-IR spectrometer 22 (CVI SM302) equipped with a thermoelectrically cooled InGaAs multichannel detector. Applicants typically used spectral integration times of 1 s and averaged 10 spectra per acquisition. The peak fluorescence wavelengths of (7,5) and (7,6) SWCNTs in the film were found by separately fitting local Gaussian functions to the emission features near 1040 and 1140 nm Applicants verified the reproducibility of results using independently prepared samples.

Results and Discussion

Figure 2:
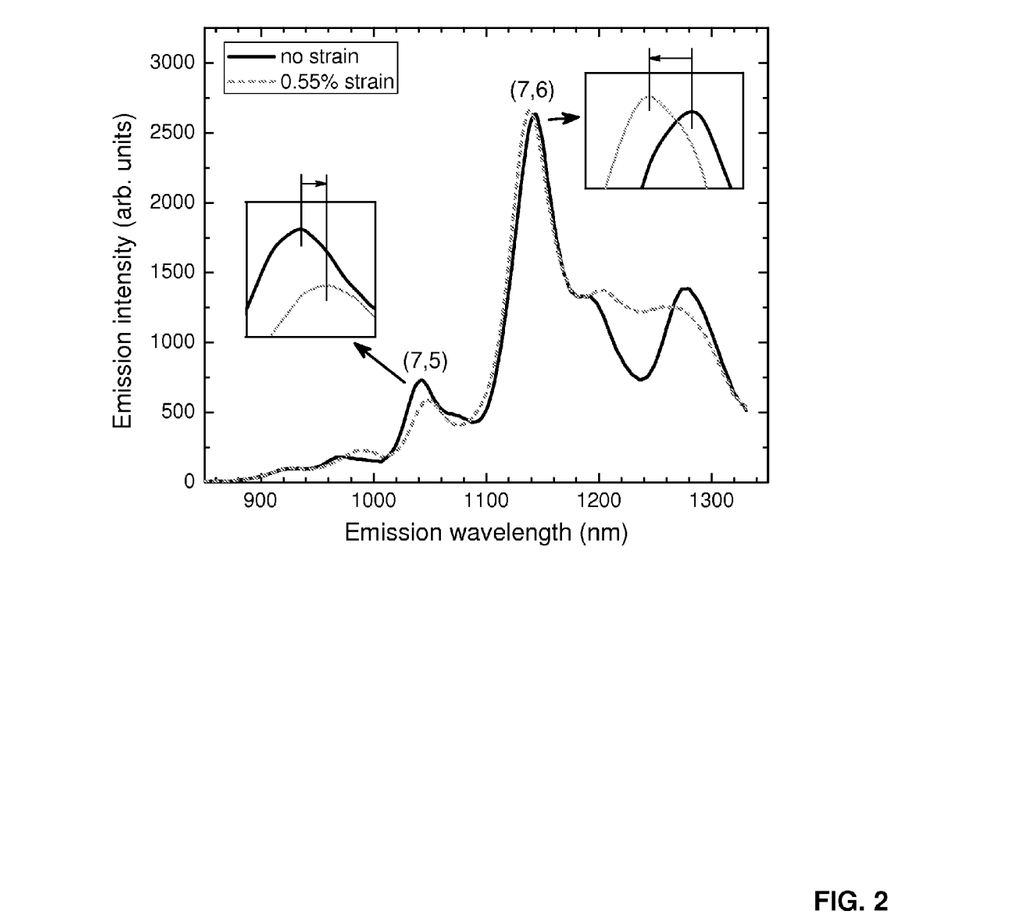
FIG. 2 provides data relating to changes in a "strain paint" emission spectrum as a function of applied strain. Emission spectra are shown for applied substrate strains of 0% (black solid line) and 0.55% (dashed line). Insets illustrate the opposite shifts in peak positions for features dominated by (7,5) and (7,6) SWCNTs.

In this Example, Applicants made a series of measurements with the samples and methods described above to demonstrate the feasibility of non-contact strain measurement using films with randomly oriented, structurally unsorted SWCNTs. FIG. 2 compares typical SWCNT emission spectra measured from the substrate surface when unstrained and when strained to 0.55% (in tension) in a direction parallel to the polarization axis of the excitation laser. It can be seen from the insets that the peaks attributed mainly to (7,5) and (7,6) SWCNTs shift in opposite directions with strain, as is expected because (7,5) is a mod 2 nanotube whereas (7,6) is mod 1. Applicants exploited this effect by tracking the difference between (7,6) and (7,5) peak wavelengths as the test plate was loaded and then unloaded. This differential shift measurement is nearly insensitive to global emission shifts caused by environmental changes, and provides higher sensitivity to strain than measurement of either individual peak position alone.

Applicants' results (FIG. 3) show linear dependences during loading and unloading, with slopes of approximately 17.2 nm/% and an average hysteresis corresponding to 0.04% strain. At high strain values, Applicants would expect nonlinearities and large irreversible properties similar to those observed in single-nanotube studies, caused by slippage of SWCNTs within the polymer film. However, the small stable hysteresis seen in FIG. 3 instead appears due to mechanical relaxation of the strained polymer film, which was approximately 20 µm thick. This effect should be reduced in films that are thinner or are prepared by more refined methods.

Figure 4:
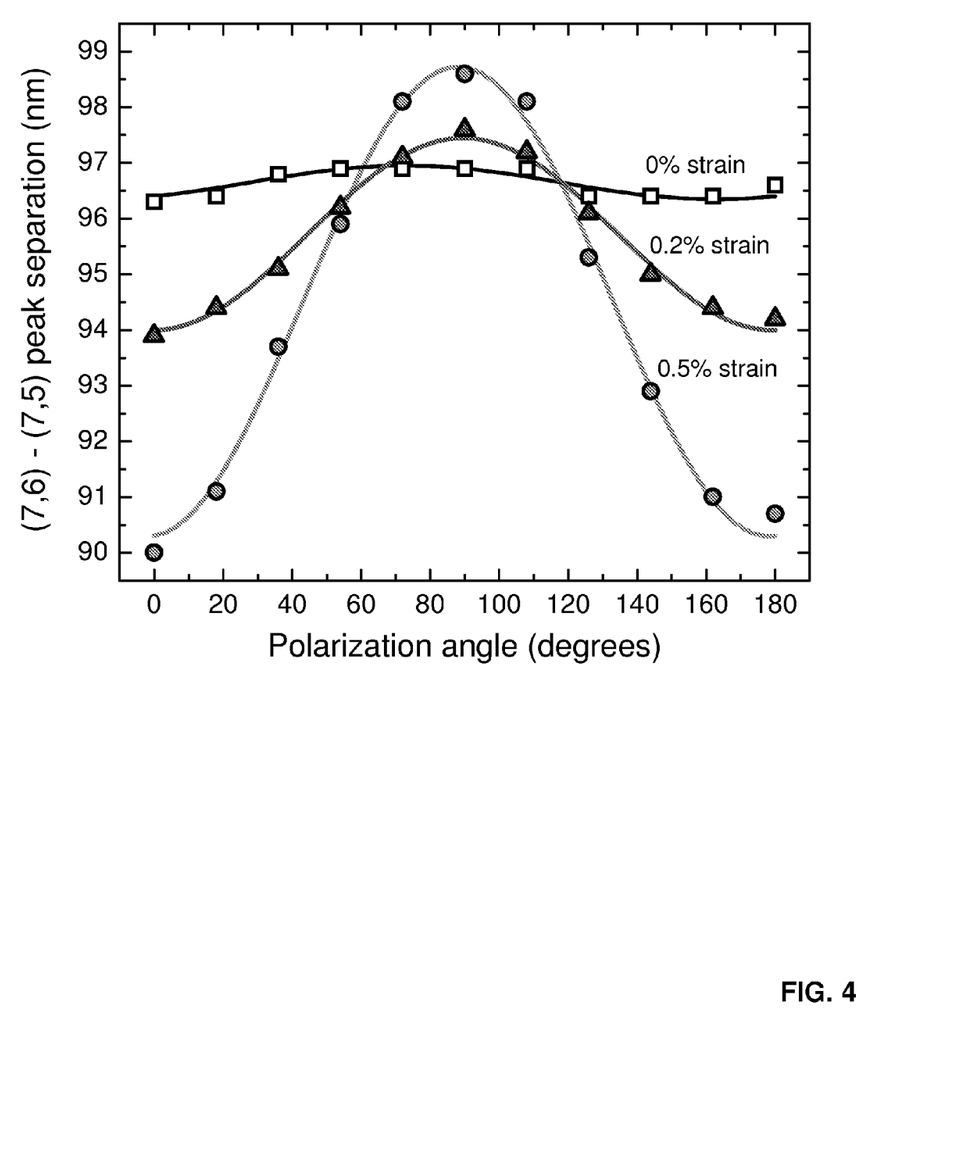
FIG. 4 provides data relating to polarization selectivity of differential spectral shift. The difference in peak emission wavelengths of (7,6) and (7,5) nanotubes in a polymeric coating is plotted against the angle between the axes of applied strain and excitation laser polarization. Applied strain magnitudes were 0 (open squares), 0.2% (triangles), and 0.5% (circles). The solid curves show best fit to the data using a $\cos^2$ function.

When linearly polarized light is used to irradiate the coated surface, emission will be strongest for those nanotubes aligned along the polarization axis, because the dominant nanotube spectral transitions are highly anisotropic. Applicants measured the dependence of the (7,6)-(7,5) peak separation on polarization angle of the excitation laser relative to the applied strain axis, with fixed strain (FIG. 4). These data can be fit well by the following function:

$$\Delta\lambda = A\cos^2(\alpha-\alpha_0)+C \qquad (1)$$

In the above formula, $\alpha$ is the laboratory angle of the laser polarization axis, $\alpha_0$ is the laboratory angle of the fixed strain axis, C is the (7,6)-(7,5) peak separation with no strain, and A is an amplitude factor equal to the peak-to-valley difference in FIG. 4. The 0.5% fit shown was computed with A=-8.4 nm, $\alpha_0$=-1.9°, and C=98.7 nm. The large modulation amplitude confirms that Applicants' method can selectively resolve and measure strains along different directions of a substrate. If necessary, directional selectivity can be further increased by using polarized detection in addition to polarized excitation.

In practical implementations of this non-contact strain sensing method, properties of the polymeric film material can be important. For instance, in some embodiments, the material must not strongly attenuate the red and near-IR wavelengths of nanotube excitation and emission transitions, and must not significantly quench the intrinsic fluorescence of embedded SWCNTs. It also needs to support dispersions of individualized SWCNTs, show strong interfacial adhesion, and provide good mechanical and environmental durability. Applicants' studies to date have found a commercial polyurethane-based varnish to be a promising material for strain paint films. Properties of the SWCNTs suspended in the film also affect the performance of Applicants' method. For instance, in some embodiments, it is desirable for the nanotubes to be nearly pristine and unbundled to give bright near-IR fluorescence, and those specific (n,m) species used in the spectral analysis should be relatively abundant. Ideal SWCNT formulations could be prepared by enriching the desired (n,m) species through sorting methods such as density gradient ultracentrifugation.

In contrast to Applicants' prior study of individual SWCNTs in a strained polymer, each spectral measurement on the coated test plate probes an ensemble of embedded SWCNTs that have random in-plane angles $\phi$ (FIGS. 1A-1B). The distribution in polar angle $\theta$ is not known a priori, because it might vary from a uniform (random) distribution to a delta function at $\theta$=90 deg (if shrinkage of the polymer film during curing forces SWCNTs to lie parallel to the substrate surface). Applicants can write the orientationally distribution function as $$f(\theta, \phi) = (1/2\pi)f(\theta).$$

If one considers an individual SWCNT in the film (FIG. 1C), the relative probability that it will absorb light from a plane-polarized excitation beam propagating along the z-axis with the polarization plane intersecting the x-y plane at an angle $\alpha$ to the x-axis is $\sin^2(\theta)\cos^2(\phi-\alpha)$. For strain applied parallel to the x-axis, the resulting spectral shift of the nanotube fluorescence, $\Delta$, will have an angular dependence $\Delta(\theta, \phi, \alpha)=\Delta_{max}(\cos^2\beta-\eta\sin^2\beta)$, where $\Delta_{max}$ is the shift for that (n,m) species when the strain is applied parallel to the tube axis, $\beta$=arccos (sin $\theta$ cos $\phi$ cos $\alpha$+sin $\theta$ sin $\phi$ sin $\alpha$) is the angle between the nanotube axis and the strain axis, and $\eta$ is Poisson's ratio for the host polymer. The two terms in $\Delta(\theta, \phi, \alpha)$ express nanotube axial strains caused by the host's x-axis and transverse (Poisson effect) deformations, respectively. The emission spectrum from each (n,m) species will be a superposition of peaks from nanotubes with various orientations and corresponding variations in intensities and strain-induced spectral shifts. Applicants can express $S(\Delta)$, the intensity-weighted distribution of spectral shifts, as follows:

$$S(\Delta) = \int_0^{2\pi}\int_0^{\pi} f(\theta, \phi)\Delta(\theta, \phi, \alpha)\sin^2(\theta)\cos^2(\phi-\alpha)\sin(\theta)d\theta d\phi, \qquad (2)$$

or $$S(\Delta) = \frac{1}{2\pi}\int_0^{2\pi}\int_0^{\pi} f(\theta)\Delta(\theta, \phi, \alpha)\sin^3(\theta)\cos^2(\phi-\alpha)d\theta d\phi. \qquad (3)$$

The above relation describes how an ensemble of orientationally distributed SWCNTs in a strained environment gives an emission spectrum that is broadened and less shifted in peak position than the same nanotubes aligned parallel to the strain axis and parallel to the surface. By evaluating equation 3 using the $\Delta_{max}$ values found from theory and prior experiments and comparing the result with the empirical slope in FIG. 3, Applicants deduce that f($\theta$), the distribution of polar angles, has a strong maximum near $\theta$=90°. This implies that SWCNTs are preferentially aligned parallel to the surface through application and curing of the polymer film.

Figure 3:
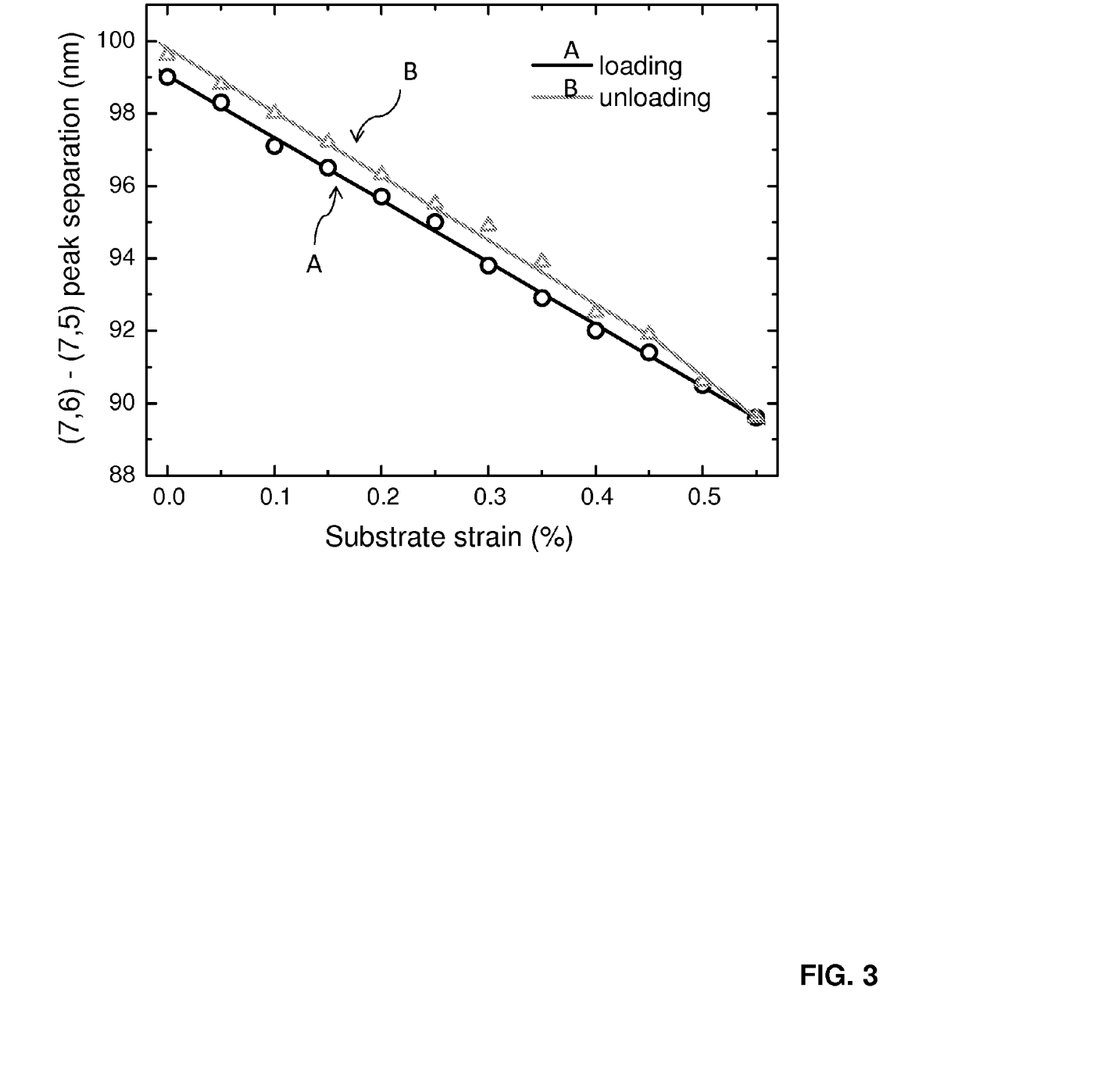
FIG. 3 provides data relating to strain variation of differential spectral shifts. The difference in peak emission wavelengths of (7,6) and (7,5) nanotubes in a polymeric coating is plotted as a function of strain in the substrate, as measured with a resistive strain gage. Circles show data measured with increasing strain. Triangles were measured with decreasing strain. Straight lines show linear best fits to the data.

Despite the formal complexities discussed above in using first principles to deduce strains from spectroscopic data on ensembles of orientationally diverse SWCNT samples, the data in FIGS. 3 and 4 demonstrate sensitivity, precision, and directional resolution that are suitable for practical applications. Applicants' method allows mapping a strain field over a wide area simply by moving the optical system to each point of interest and capturing emission spectra for several polarization settings of the excitation beam. The grid used in such strain mapping can be as coarse or fine as desired, because the SWCNT sensors are homogeneous throughout the coating. Absolute strain values can be found by applying empirical calibrations determined for the relevant strain paint formulations and application methods. Although the present results have been obtained with laboratory instrumentation, it seems likely that the necessary optical and computer hardware can be integrated into a field-portable strain reader that could capture and analyze spectra even faster than the few seconds used to acquire data points in this study. Applicants expect that the method described here will enable practical non-contact strain measurements and allow improved structural health monitoring in aerospace and civil engineering.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of detecting strain associated with an object, said method comprising:
   irradiating a composition that has been applied to the object,
      wherein the composition comprises semiconducting single-walled carbon nanotubes;
   measuring an emission from the irradiated composition,
      wherein the emission comprises near infrared emission; and
   correlating the near infrared emission to the presence or absence of strain associated with the object, wherein the steps of irradiating, measuring and correlating occur without physically contacting the object or the composition.

2. The method of claim 1, wherein the method occurs without utilizing Raman spectroscopy.

3. The method of claim 1, wherein the irradiating occurs by use of a light source.

4. The method of claim 3, wherein the light source is selected from the group consisting of lasers, light emitting diodes, incoherent light, polarized light, unpolarized light, and combinations thereof.

5. The method of claim 4, wherein the light source comprises polarized light.

6. The method of claim 1, wherein the measuring of the emission occurs by optical infrared spectrometry.

7. The method of claim 1, wherein the presence or absence of strain is determined as a function of a spectral shift of the semiconducting single-walled carbon nanotubes in the composition, wherein the spectral shift is indicative of strain.

8. The method of claim 7, wherein the spectral shift comprises a spectral shift in an emission peak of the carbon nanotubes.

9. The method of claim 1, wherein the object is selected from the group consisting of concrete, steel, metals, alloys, non-metallic composites, pipes, pavements, vessels, engines, optical fibers, and combinations thereof.

10. The method of claim 1, further comprising a step of applying the composition to the object.

11. The method of claim 10, wherein the applying comprises at least one of spraying, coating, spray coating, shift coating, spin coating, dip coating, printing, brushing, and combinations thereof.

12. The method of claim 1, wherein the composition is applied to a surface of the object, and wherein the presence or absence of strain is determined on the surface of the object.

13. The method of claim 1, wherein the composition is applied to an internal cavity of an object, and wherein the strain is determined on the internal cavity of the object.

14. The method of claim 1, wherein the composition is applied to an edge of an object, and wherein the strain is determined on the edge of the object.

15. The method of claim 1, wherein the semiconducting single-walled carbon nanotubes in the composition comprise pristine single-walled carbon nanotubes.

16. The method of claim 1, wherein the semiconducting single-walled carbon nanotubes in the composition comprise functionalized single-walled carbon nanotubes.

17. The method of claim 16, wherein the semiconducting single-walled carbon nanotubes are functionalized with one or more functionalizing agents.

18. The method of claim 16, wherein the functionalizing agents are selected from the group consisting of phenyl groups, aniline groups, alkanes, alkyl groups, aryl groups, tert-butyl groups, alkenyl groups, alkynyl groups, ester groups, carboxyl groups, halogens, metals, metal oxides, metal sulfides, sulfate groups, and combinations thereof.

19. The method of claim 1, wherein the semiconducting single-walled carbon nanotubes in the composition comprise structurally selected single-walled carbon nanotubes.

20. The method of claim 19, wherein the semiconducting single-walled carbon nanotubes are structurally selected based on chirality, length, diameter, and combinations thereof.

21. The method of claim 20, wherein the semiconducting single-walled carbon nanotubes in the composition are structurally selected based on chirality.

22. The method of claim 19, wherein the semiconducting single-walled carbon nanotubes in the composition are structurally selected based on (n, m) structures.

23. The method of claim 1, wherein the semiconducting single-walled carbon nanotubes in the composition comprise individualized single-walled carbon nanotubes.

24. The method of claim 1, wherein the semiconducting single-walled carbon nanotubes are randomly dispersed in the composition.

25. The method of claim 1, wherein the semiconducting single-walled carbon nanotubes are uni-directionally aligned in the composition.

26. The method of claim 1, wherein the composition further comprises a polymer.

27. The method of claim 26, wherein the polymer is selected from the group consisting of polyethylenes, polypropylenes, polystyrenes, polyamides, polyimides, epoxies, polyvinyl alcohols, polybutadienes, poly acrylic acids, poly lactic acids, poly methacrylic acids, polymethyl methacrylates, polyurethanes, poly vinyl chlorides, polycarbonates, cyanoacrylates and combinations thereof.

28. The method of claim 26, wherein the polymer comprises polyurethane.

29. The method of claim 1, wherein the composition that is applied to the object has a thickness that ranges from about 1 μm to about 1 mm.

30. The method of claim 1, wherein the composition that is applied to the object has a thickness that ranges from about 10 μm to about 500 μm.

31. The method of claim 1, wherein the composition that is applied to the object has a thickness of about 25 μm.

32. The method of claim 1, wherein the method is utilized to detect strains of less than about 1%.

* * * * *